US012292444B2

United States Patent
Uversky et al.

(10) Patent No.: US 12,292,444 B2
(45) Date of Patent: May 6, 2025

(54) METHODS AND COMPOSITIONS RELATED TO MODIFIED GREEN FLUORESCENT PROTEIN (GFP) WITH AN EMBEDDED FOREIGN PEPTIDE

(71) Applicant: University of South Florida, Tampa, FL (US)

(72) Inventors: Vladimir N. Uversky, Tampa, FL (US); Bogdan S. Melnik, Pushchino (RU)

(73) Assignee: University of South Florida, Tampa, FL (US)

( * ) Notice: Subject to any disclaimer, the term of this patent is extended or adjusted under 35 U.S.C. 154(b) by 482 days.

(21) Appl. No.: 17/219,119

(22) Filed: Mar. 31, 2021

(65) Prior Publication Data

US 2021/0311068 A1 Oct. 7, 2021

Related U.S. Application Data (60) Provisional application No. 63/003,572, filed on Apr. 1, 2020.

(51) Int. Cl.
| | | |
|---|---|---|
| G01N 33/58 | (2006.01) | |
| G01N 33/50 | (2006.01) | |
| G01N 33/542 | (2006.01) | |
| G01N 33/68 | (2006.01) | |

(52) U.S. Cl.
CPC ....... *G01N 33/582* (2013.01); *G01N 33/5041* (2013.01); *G01N 33/542* (2013.01); *G01N 33/6842* (2013.01)

(58) Field of Classification Search
CPC ............. G01N 33/582; G01N 33/5041; G01N 33/542; G01N 33/6842; A61K 38/00; A61K 49/0047; C07K 14/43595
See application file for complete search history.

(56) References Cited

U.S. PATENT DOCUMENTS

| | | |
|---|---|---|
| 5,777,079 A | 7/1998 | Tsien et al. |
| 2009/0170721 A1 | 7/2009 | Waldo et al. |

FOREIGN PATENT DOCUMENTS

| | | |
|---|---|---|
| WO | 98/06737 | 2/1998 |

OTHER PUBLICATIONS

UniProt; https://www.uniprot.org/uniprotkb/P42212/entry; accessed on Jul. 10, 2023 (Year: 1995).*
Protein DabaBank; https://www.rcsb.org/sequence/1B9C; accessed Jul. 11, 2023 (Year: 2000).*
Flores-Ramírez, Gabriela, et al. "The effect of amino acid deletions and substitutions in the longest loop of GFP." BMC chemical biology 7.1 (2007): 1-10. (Year: 2007).*

(Continued)

*Primary Examiner* — Louise W Humphrey
*Assistant Examiner* — Candice Lee Swift
(74) *Attorney, Agent, or Firm* — Meunier Carlin & Curfman LLC (57) ABSTRACT

Disclosed herein are methods and compositions comprising chimeric green fluorescent protein (GFP) molecules embedded with foreign molecules. Also disclosed are methods of treating a subject with chimeric GFP molecules embedded with foreign molecules. Further disclosed are methods of delivering a desired molecule to a cell, wherein said desired molecule is embedded within a chimeric GFP molecule.

4 Claims, 3 Drawing Sheets
Specification includes a Sequence Listing.

A

B bactenecin        RLC (56) References Cited

OTHER PUBLICATIONS

Hoffman RM. Application of GFP imaging in cancer. Lab Invest. Apr. 2015;95(4):432-52. doi: 10.1038/labinvest.2014.154. Epub Feb. 16, 2015. PMID: 25686095; PMCID: PMC4383682. (Year: 2015).*
Glukhova, K. A., V. G. Klyashtorny, and B. S. Melnik. "GFP fusion protein with embedded foreign peptide." bioRxiv (2019): 855908. (Year: 2019).*
The Amino Company; https://aminoco.com/blogs/amino-acids/what-are-hydrophilic-amino-acids accessed Jul. 10, 2023 (Year: 2019).*
Wachter, Rebekka M., et al. "Crystal structure and photodynamic behavior of the blue emission variant Y66H/Y145F of green fluorescent protein." Biochemistry 36.32 (1997): 9759-9765. (Year: 1997).*
Allucent; https://www.allucent.com/resources/blog/points-consider-drug-development-biologics-and-small-molecules; accessed Nov. 28, 2023 (Year: 2023).*
Shadidi, Mohsen, and Mouldy Sioud. "Identification of novel carrier peptides for the specific delivery of therapeutics into cancer cells ." The FASEB Journal 17.2 (2003): 256-258. (Year: 2003).*
Takahashi, Tsuyoshi, Kenichi Ohta, and Hisakazu Mihara. "Embedding the Amyloid β-Peptide Sequence in Green Fluorescent Protein Inhibits Aβ Oligomerization." ChemBioChem 8.9 (2007): 985-988. (Year: 2007).*
Brogden, Kim A., et al. "Antimicrobial peptides in animals and their role in host defences." International journal of antimicrobial agents 22.5 (2003): 465-478. (Year: 2003).*
Young-Speirs, Morgan, et al. "Host defense cathelicidins in cattle: types, production, bioactive functions and potential therapeutic and diagnostic applications." International journal of antimicrobial agents 51.6 (2018): 813-821. (Year: 2018).*
Van Staden, Anton Du Preez, et al. "Functional expression of GFP-fused class I lanthipeptides in Escherichia coli." ACS Synthetic Biology 8.10 (2019): 2220-2227. (Year: 2019).*
Nischan, Nicole, et al. "Covalent attachment of cyclic TAT peptides to GFP results in protein delivery into live cells with immediate bioavailability." Angewandte Chemie International Edition 54.6 (2015): 1950-1953. (Year: 2015).*
Abedi, M. R., Caponigro, G., & Kamb, A. (1998). Green fluorescent protein as a scaffold for intracellular presentation of peptides. Nucleic Acids Research, 26(2), 623-630. doi: 10.1093/nar/26.2.623.
Abraham, Mark James, et al. "GROMACS: High performance molecular simulations through multi-level parallelism from laptops to supercomputers." SoftwareX 1 (2015): 19-25. doi: 10.1016/j.softx.2015.06.001.
Battistutta, Roberto, Alessandro Negro, and Giuseppe Zanotti. "Crystal structure and refolding properties of the mutant F99S/M153T/V163A of the green fluorescent protein." Proteins: Structure, Function, and Bioinformatics 41.4 (2000): 429-437. doi: 10.1002/1097-0134(20001201)41.
Bokman, Stephen H., and William W. Ward. "Renaturation of Aequorea green- fluorescent protein." Biochemical and biophysical research communications 101.4 (1981): 1372-1380. doi: 10.1016/0006-291X(81)91599-0.
Cody, Chris W., et al. "Chemical structure of the hexapeptide chromophore of the Aequorea green-fluorescent protein." Biochemistry 32.5 (1993): 1212-1218.
Dosztányi, Zsuzsanna, et al. "IUPred: web server for the prediction of intrinsically unstructured regions of proteins based on estimated energy content." Bioinformatics 21.16 (2005): 3433-3434.
Glukhova, Kseniya F., et al. "Isoforms of green fluorescent protein differ from each other in solvent molecules 'trapped' inside this protein." Journal of Biomolecular Structure and Dynamics 35.6 (2017): 1215-1225. doi: 10.1080/07391102.2016.1174737.
Hancock, Robert EW, Evan F. Haney, and Erin E. Gill. "The immunology of host defence peptides: beyond antimicrobial activity." Nature Reviews Immunology 16.5 (2016): 321-334 . . . doi: 10.1038/nri.2016.29.
Hoffman, Robert M. "Application of GFP imaging in cancer." Laboratory investigation 95.4 (2015): 432-452.
Kent, Kevin P., Luke M. Oltrogge, and Steven G. Boxer. "Synthetic control of green fluorescent protein." Journal of the American Chemical Society 131.44 (2009): 15988-15989. doi: 10.1021/ja906303f.
Li, Xiaohong, et al. "Predicting protein disorder for N-, C-and internal regions." Genome Informatics 10 (1999): 30-40.
Li, Yifeng. "Carrier proteins for fusion expression of antimicrobial peptides in Escherichia coli." Biotechnology and applied biochemistry 54.1 (2009): 1-9.doi: 10.1042/BA20090087.
Melnik, Tatiana N., et al. "Multi-state proteins: approach allowing experimental determination of the formation order of structure elements in the green fluorescent protein." PloS one 7.11 (2012): e48604.doi: 10.1371/journal.pone.0048604.
Mészáros, Bálint, Gábor Erdős, and Zsuzsanna Dosztányi. "IUPred2A: context-dependent prediction of protein disorder as a function of redox state and protein binding." Nucleic acids research 46.W1 (2018): W329-W337.
Obradovic, Zoran, et al. "Exploiting heterogeneous sequence properties improves prediction of protein disorder." Proteins: Structure, Function, and Bioinformatics 61.S7 (2005): 176-182.
Ormö, Mats, et al. "Crystal structure of the Aequorea victoria green fluorescent protein." Science 273.5280 (1996): 1392-1395.doi: 0.1126/science.273.5280.1392.
Paschke, M., Tiede, C., & Höhne, W. (2007). Engineering a circularly permuted GFP scaffold for peptide presentation. Journal of Molecular Recognition, 20(5), 367-378. doi: 10.1002/jmr.844.
Peng, Kang, et al. "Length-dependent prediction of protein intrinsic disorder." BMC bioinformatics 7.1 (2006): 1-17, 208.
Peng, Kang, et al. "Optimizing long intrinsic disorder predictors with protein evolutionary information." Journal of bioinformatics and computational biology 3.01 (2005): 35-60.
Prasher, Douglas C., et al. "Primary structure of the Aequorea victoria green-fluorescent protein." Gene 111.2 (1992): 229-233.
Romero, Pedro, et al. "Sequence complexity of disordered protein." Proteins: Structure, Function, and Bioinformatics 42.1 (2001): 38-48.
Silverman, The Organic Chemistry of Drug Design and Drug Action, pp. 352-401, Academic Press, San Diego, Calif. (1992).
Soundrarajan N, Cho HS, Ahn B, et al. Green fluorescent protein as a scaffold for high efficiency production of functional bacteriotoxic proteins in Escherichia coli. Sci Rep. 2016;6:20661. Published Feb. 11, 2016. doi:10.1038/srep20661.
Stepanenko, Olesya V., et al. "Beta-barrel scaffold of fluorescent proteins: folding, stability and role in chromophore formation." International review of cell and molecular biology 302 (2013): 221-278. doi: 10.1016/B978-0-12-407699-0.00004-2.
Tsien, Roger Y. "The green fluorescent protein." Annual review of biochemistry 67.1 (1998): 509-544.
Urban, Patricia, et al. "Nanotools for the delivery of antimicrobial peptides." Current drug targets 13.9 (2012): 1158-1172. doi: 10.2174/138945012802002302.
Wang, R., Xiang, S., Zhang, Y., Chen, Q., Zhong, Y., & Wang, S. (2014). Development of a Functional Antibody by Using a Green Fluorescent Protein Frame as the Template. Applied and Environmental Microbiology, 80(14), 4126-4137. doi: 10.1128/aem.00936-14.
Wu, Manhong, and Robert EW Hancock. "Improved derivatives of bactenecin, a cyclic dodecameric antimicrobial cationic peptide." Antimicrobial agents and chemotherapy 43.5 (1999): 1274-1276. doi: 10.1074/jbc.274.1.29.
Xue, Bin, et al. "PONDR-FIT: a meta-predictor of intrinsically disordered amino acids." Biochimica et Biophysica Acta (BBA)-Proteins and Proteomics 1804.4 (2010): 996-1010.
Yang, Fan, Larry G. Moss, and George N. Phillips. "The molecular structure of green fluorescent protein." Nature biotechnology 14.10 (1996): 1246-1251.

* cited by examiner

SEQUENCE LISTING

```
<160> NUMBER OF SEQ ID NOS: 5

<210> SEQ ID NO 1
<211> LENGTH: 16
<212> TYPE: PRT
<213> ORGANISM: Aequorea victoria

<400> SEQUENCE: 1

Arg Leu Cys Arg Ile Val Ser Tyr Gly Val Ile Arg Val Cys Arg Arg
1               5                   10                  15

<210> SEQ ID NO 2
<211> LENGTH: 238
<212> TYPE: PRT
<213> ORGANISM: Aequorea victoria

<400> SEQUENCE: 2

Met Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
                20                  25                  30

Gly Glu Gly Asp Ala Thr Tyr Gly Lys Leu Thr Leu Lys Phe Ile Cys
            35                  40                  45

Thr Thr Gly Lys Leu Pro Val Pro Trp Pro Thr Leu Val Thr Thr Phe
        50                  55                  60

Ser Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Met Ala Asp Lys Gln Lys Asn Gly
145                 150                 155                 160

Ile Lys Val Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235
```

<210> SEQ ID NO 3
<211> LENGTH: 239
<212> TYPE: PRT
<213> ORGANISM: Aequorea victoria

<400> SEQUENCE: 3

Met Ser Lys Gly Glu Glu Leu Ile Thr Gly Val Val Pro Ile Leu Val
1               5                   10                  15

Glu Leu Asp Gly Asp Val Asn Gly His Lys Phe Ser Val Ser Gly Glu
                20                  25                  30

Gly Glu Gly Asp Ala Thr Tyr Gly Lys Leu Thr Leu Lys Phe Ile Cys
            35                  40                  45

Thr Thr Gly Lys Leu Pro Val Pro Trp Pro Arg Leu Cys Arg Ile Val
        50                  55                  60

Ser Tyr Gly Val Ile Arg Val Cys Arg Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
                100                 105                 110

Val Lys Phe Glu Gly Asp Thr Leu Val Asn Arg Ile Glu Leu Lys Gly
            115                 120                 125

Ile Asp Phe Lys Glu Asp Gly Asn Ile Leu Gly His Lys Leu Glu Tyr
130                 135                 140

Asn Tyr Asn Ser His Asn Val Tyr Ile Met Ala Asp Lys Gln Lys Asn
145                 150                 155                 160

Gly Ile Lys Val Asn Phe Lys Ile Arg His Asn Ile Glu Asp Gly Ser
                165                 170                 175

Val Gln Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
210                 215                 220

Val Thr Ala Ala Gly Ile Thr His Gly Met Asp Glu Leu Tyr Lys
225                 230                 235

<210> SEQ ID NO 4
<211> LENGTH: 238
<212> TYPE: PRT
<213> ORGANISM: Aequorea victoria

<400> SEQUENCE: 4

Met Ser Lys Gly Glu Glu Leu Asp Thr Gly Val Val Pro Ile Leu Val
1               5                   10                  15

Glu Leu Asp Gly Asp Val Asn Gly His Lys Phe Ser Val Ser Gly Glu
                20                  25                  30

Gly Glu Gly Asp Ala Thr Tyr Gly Lys Leu Thr Leu Lys Phe Ile Cys
            35                  40                  45

Thr Thr Gly Lys Leu Pro Val Pro Trp Pro Thr Leu Val Thr Thr Phe
        50                  55                  60

Ser Tyr Gly Val Gln Cys Phe Ser Arg Tyr Pro Asp His Met Lys Gln
65                  70                  75                  80

His Asp Phe Phe Lys Ser Ala Met Pro Glu Gly Tyr Val Gln Glu Arg
                85                  90                  95

Thr Ile Phe Phe Lys Asp Asp Gly Asn Tyr Lys Thr Arg Ala Glu Val

```
            100                 105                 110
Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
        130                 135                 140

Tyr Asn Ser His Asn Val Tyr Ile Met Ala Asp Lys Gln Lys Asn Gly
145                 150                 155                 160

Ile Lys Val Asn Phe Lys Asp Arg His Asn Ile Glu Asp Gly Ser Val
                165                 170                 175

Glu Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
        210                 215                 220

Thr Ala Ala Gly Ile Thr His Gly Met Asp Glu Leu Tyr Lys
225                 230                 235

<210> SEQ ID NO 5
<211> LENGTH: 239
<212> TYPE: PRT
<213> ORGANISM: Aequorea victoria

<400> SEQUENCE: 5

Met Ser Lys Gly Glu Glu Leu Asp Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Arg Leu Cys Arg Ile Val
    50                  55                  60

Ser Tyr Gly Val Ile Arg Val Cys Arg Arg Tyr Pro Asp His Met Lys
65                  70                  75                  80

Gln His Asp Phe Phe Lys Ser Ala Met Pro Glu Gly Tyr Val Gln Glu
                85                  90                  95

Arg Thr Ile Phe Phe Lys Asp Asp Gly Asn Tyr Lys Thr Arg Ala Glu
            100                 105                 110

Val Lys Phe Glu Gly Asp Thr Leu Val Asn Arg Ile Glu Leu Lys Gly
        115                 120                 125

Ile Asp Phe Lys Glu Asp Gly Asn Ile Leu Gly His Lys Leu Glu Tyr
    130                 135                 140

Asn Tyr Asn Ser His Asn Val Tyr Ile Met Ala Asp Lys Gln Lys Asn
145                 150                 155                 160

Gly Ile Lys Val Asn Phe Lys Asp Arg His Asn Ile Glu Asp Gly Ser
                165                 170                 175

Val Glu Leu Ala Asp His Tyr Gln Gln Asn Thr Pro Ile Gly Asp Gly
            180                 185                 190

Pro Val Leu Leu Pro Asp Asn His Tyr Leu Ser Thr Gln Ser Ala Leu
        195                 200                 205

Ser Lys Asp Pro Asn Glu Lys Arg Asp His Met Val Leu Leu Glu Phe
    210                 215                 220

Val Thr Ala Ala Gly Ile Thr His Gly Met Asp Glu Leu Tyr Lys
225                 230                 235
```

METHODS AND COMPOSITIONS RELATED TO MODIFIED GREEN FLUORESCENT PROTEIN (GFP) WITH AN EMBEDDED FOREIGN PEPTIDE

CROSS-REFERENCE TO RELATED APPLICATIONS

This application claims benefit of U.S. Provisional Application No. 63/003,572, filed Apr. 1, 2020, incorporated herein by reference in its entirety.

BACKGROUND

Antimicrobial peptides (AMPs) are amphipathic molecules consisting mainly of positively charged and hydrophobic amino acids. AMPs interact with negatively charged phospholipids of bacterial plasma membrane and form pores in the membrane, which leads to the loss of membrane integrity resulting in cell death. These peptides affect a wide range of pathogens, such as bacteria, fungi, and viruses (Hancock 2016). Studying AMPs and their therapeutic implementation is limited by a number of problems related to their production and application. For instance, antibacterial activity impedes their production in bacterial culture. Alternative production pathways, such as eukaryotic producers, chemical synthesis or isolation from natural sources, increase the production costs significantly. Modern approaches are based on decreasing AMP toxicity via their synthesis in inactive form. In this way, the peptides are produced in bacterial culture in form of chimeric proteins where auxiliary proteins or peptides (thioredoxin, SUMO, PurF, etc.) neutralize the toxicity of AMPs (Li 2009). Another problem is related to fast degradation of the peptides after their injection into the organism. To address this problem, variants of peptide protection via their encapsulation into liposomes and polymeric particles have been proposed (Urban 2012).

Green fluorescent protein (GFP) is a 238-residue-long globular protein folded into a β-barrel consisting of eleven antiparallel β-strands linked by loops and five short α-helices. The β-barrel represents a cylinder, inside of which an α-helix with the covalently bonded chromophore, 4-(p-hydroxybenzylidene) imidazolidin-5-one (HBI) is placed. The β-barrel serves as a natural protector for the chromophore from fluorescence quenchers and proteases. GFP is known to be resistant to proteases (Bokman 1981). Despite its tight packing, free space exists inside the protein, where water molecules can be detected (Ormo 1996). Also, salt ions can be retained inside GFP (Glukhova 2017). The microenvironment of the chromophore is rich in charged amino acid residues, with some of them being responsible for ion retention inside the barrel. Kent et al. attempted to substitute the central α-helix of GFP for the xenogenic α-helical peptide (Kent 2009). The authors had successfully replaced the central α-helix and showed that the proteins remained structured, and fluorescence of mature chromophores was observed. However, what is needed in the art is a complete system for synthesis and targeting of peptides suitable for practical applications.

SUMMARY

Disclosed herein is a composition comprising a modified green fluorescent protein (GFP) molecule and a non-native molecule, wherein the non-native molecule is embedded within the modified GFP molecule. One or more amino acids within the modified GFP molecule can be modified in order to confer stability to composition. For example, one or more modified amino acids can comprise one or more amino acid substitutions, such as hydrophobic amino acids. The one or more amino acid substitutions can comprise at least one of F8D, Q177E, or I167D in SEQ ID NO: 2.

When expressed, the non-native molecule can be embedded within β-barrel region of the modified GFP. The non-native molecule can be inserted into central α-helix region of the modified GFP. The non-native molecule can be a therapeutic, diagnostic, or prophylactic molecule. For example, the non-native molecule can comprise one or more of an antineoplastic agent, an immunomodulating agent, a neuroactive agent, an anti-inflammatory agent, an antilipidemic agent, a hormone, a receptor agonist or antagonist, or an anti-infective agent, or a compound selected from a protein, a peptide, an antibody, an enzyme, a hormone, a cofactor, a steroid, a detection agent, an imaging agent, a contrast agent, a gas, a pharmaceutically-active molecule, or a combination thereof. The modified GFP molecule can be capable of fluorescence.

Also disclosed is a nucleic acid encoding a modified GFP molecule and a non-native peptide, wherein said non-native peptide is within the central α-helical moiety of GFP. At least a part of the α-helical moiety of naturally occurring GFP is replaced with a non-native peptide. Also disclosed is a cell encoding the nucleic acid.

Further disclosed is a method for treating a subject in need thereof, the method comprising administering to the subject a composition comprising a modified GFP molecule and a non-native molecule, wherein the non-native molecule is embedded within the modified GFP molecule, and further wherein the non-native molecule is useful in treating the subject. One or more of the amino acids within the modified GFP molecule can be modified in order to confer stability to composition. The modified GFP molecule can be capable of fluorescence, thereby enabling simultaneous detection and treatment.

Disclosed herein is a method for delivering a desired molecule to a cell, the method comprising exposing the cell to a composition comprising a modified GFP molecule and a non-native molecule, wherein the non-native molecule is embedded within the modified GFP molecule. This method can be done in vivo or in vitro.

BRIEF DESCRIPTION OF THE FIGURES

The accompanying drawings, which are incorporated in and constitute a part of this specification, illustrate certain examples of the present disclosure and together with the description, serve to explain, without limitation, the principles of the disclosure. Like numbers represent the same elements throughout the figures.

FIG. 1A-B shows (A) 3D structure of GFP (PDB ID: 1B9C). (B) Sequence alignment of bactenecin (residues 1-6 and 10-15 of SEQ ID NO: 1), GFP central α-helix (residues 59-73 of SEQ ID NO: 3), and GFP-bactenecin hybrid protein (residues 1-15 of SEQ ID NO: 1). Hydrophobic amino acids are highlighted in gray.

FIG. 2 shows an electrophoregram of the cell samples producing GFP-bactenecin.

1—cells before induction by IPTG;
2—cells after 2 hours of induction by IPTG;
3—cells after 4 hours of induction by IPTG;
4—soluble protein fraction;
5—insoluble protein fraction.

FIG. 4A-D shows the effects of the bactenecin insertion and the F8D, I167D, and Q177E mutations on the intrinsic disorder predisposition of GFP. Intrinsic disorder profiles were generated for natural GFP (A), GFP-bactenicin (B) and optimized GFP-bactenicin with F8D, I167D, and Q177E mutations (C) by PONDR® VLXT (black curves), PONDR® VL3 (red curves), PONDR® VSL2 (green curves), PONDR® FIT (pink curves), IUPred_short (yellow curves), and IUPred_long (blue curves). Dark cyan dashed lines show the mean disorder propensity calculated by averaging disorder profiles of individual predictors. Light pink and light cyan shadows around the PONDR® FIT and mean disorder curves represent distribution of errors. Plot D compares profiles generated for these three proteins by PONDR® VLXT.

DETAILED DESCRIPTION

Definitions

In this specification and in the claims which follow, reference will be made to a number of terms which shall be defined to have the following meanings:

Ranges can be expressed herein as from "about" one particular value, and/or to "about" another particular value. When such a range is expressed, another example includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular electrode is disclosed and discussed and a number of modifications that can be made to the electrode are discussed, specifically contemplated is each and every combination and permutation of the electrode and the modifications that are possible unless specifically indicated to the contrary. Thus, if a class of electrodes A, B, and C are disclosed as well as a class of electrodes D, E, and F and an example of a combination electrode, or, for example, a combination electrode comprising A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

It is understood that the compositions disclosed herein have certain functions. Disclosed herein are certain structural requirements for performing the disclosed functions, and it is understood that there are a variety of structures which can perform the same function which are related to the disclosed structures, and that these structures will ultimately achieve the same result.

As used in the specification and claims, the singular form "a", "an" and "the" include plural references unless the context clearly dictates otherwise.

"Comprising" refers to compounds, compositions and methods including the recited elements, but not exclude others. "Consisting essentially of," when used to define compounds, compositions or methods, shall mean excluding other elements that would materially affect the basic and novel characteristics of the claimed technology. "Consisting of," shall mean excluding any element, step, or ingredient not specified in the claim. Embodiments defined by each of these transition terms are within the scope of this technology.

As used herein, "therapeutic agent" refers to a compound, mixture of compounds, or biologic agent that can provide a beneficial effect when administered to a patient.

As used herein, "amino acid" refers to a compound containing both amino (—NH2) and carboxyl (—COOH) groups generally separated by one carbon atom. The central carbon atom may contain a substituent which can be either charged, ionisable, hydrophilic or hydrophobic. Any of 22 basic building blocks of proteins having the formula NH2-CHR—COOH, where R is different for each specific amino acid, and the stereochemistry is in the 'L' configuration. Additionally, the term "amino acid" can optionally include those with an unnatural 'D' stereochemistry and modified forms of the 'D' and 'L' amino acids.

As used herein, "peptide" refers to a chain of amino acids in which each amino acid is connected to the next by a formation of an amide bond. Peptides are generally considered to consist of up to 30 amino acids, or alternatively up to 25 amino acids, or alternatively up to 20 amino acids, or alternatively up to 15 amino acids, or alternatively up to 10 amino acids, or alternatively up to 5 amino acids, or alternatively between about 5-10 amino acids, or alternatively between about 10-15 amino acids, while the term "protein" is applied to compounds containing longer amino acid chains.

As used herein, the term "drug" refers to a pharmacologically active substance or substances that are used to diagnose, treat, or prevent diseases or conditions. Drugs act by altering the physiology of a living organism, tissue, cell, or in vitro system that they are exposed to. It is intended that the term encompass antimicrobials, including, but not limited to, antibacterial, antifungal, and antiviral compounds. It is also intended that the term encompass antibiotics, including naturally occurring, synthetic, and compounds produced by recombinant DNA technology. It is also intended to include any other drug used for the treatment or prevention of diseases or disorders, as discussed herein.

As used herein the term "prodrug" refers to a pharmacologically inactive derivative of a parent drug molecule that requires biotransformation (e.g., either spontaneous or enzymatic) within the organism to release the active drug. Preferred prodrugs are variations or derivatives of the compounds that have groups cleavable under metabolic conditions. For example, prodrugs become pharmaceutically active in vivo when they undergo solvolysis under physiological conditions or undergo enzymatic degradation or other biochemical transformation (e.g., phosphorylation, hydrogenation, dehydrogenation, glycosylation etc). Prodrugs often offer advantages of solubility, tissue compatibility, or delayed release in the mammalian organism. (See e.g., Bundgard, Design of Prodrugs, pp. 7-9, 21-24, Elsevier, Amsterdam [1985]; and Silverman, The Organic Chemistry of Drug Design and Drug Action, pp. 352-401, Academic Press, San Diego, Calif. [1992]). Common prodrugs include acid derivatives such as, esters prepared by reaction of parent acids with a suitable alcohol, amides prepared by reaction of the parent acid compound with an amine, or basic groups reacted to form an acylated base derivative. Moreover, the prodrug derivatives of this invention may be combined with other commonly known pharmacological molecules and reaction schemes to enhance bioavailability.

A "pharmaceutical composition" is intended to include the combination of an active agent with a carrier, inert or active, making the composition suitable for diagnostic or therapeutic use in vivo, in vitro or ex vivo.

As used herein, the term "pharmaceutically acceptable carrier" encompasses any of the standard pharmaceutical carriers, such as a phosphate buffered saline solution, water, and an emulsion, such as an oil/water or water/oil emulsion, and various types of wetting agents. The compositions also can include stabilizers and preservatives. For examples of carriers, stabilizers and adjuvants see Martin, Remington's Pharmaceutical Sciences, Gennaro A R ed. 20th edition, 2000: Williams & Wilkins P A, USA.

"Pharmaceutically acceptable salt" as used herein, relates to any pharmaceutically acceptable salt (acid or base) of a compound of the present invention which, upon administration to a recipient, is capable of providing a compound of this invention or an active metabolite or residue thereof. As is known to those of skill in the art, "salts" of the compounds of the present invention may be derived from inorganic or organic acids and bases. Examples of acids include hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic and benzenesulfonic acid. Other acids, such as oxalic, while not in themselves pharmaceutically acceptable, may be employed in the preparation of salts useful as intermediates in obtaining the compounds of the invention and their pharmaceutically acceptable acid.

By "green fluorescent protein" or "GFP" herein is meant a protein with at least 80% sequence identity to GFP and exhibits fluorescence at 490 to 600 nm. The wild-type GFP is 238 amino acids in length (SEQ ID NO: 2), contains a modified tripeptide fluorophore buried inside a relatively rigid β-can structure which protects the fluorophore from the solvent, and thus solvent quenching. See Prasher et al., Gene 111 (2): 229-233 (1992); Cody et al., Biochem. 32 (5): 1212-1218 (1993); Ormo et al, Science 273:1392-1395 (1996); and Yang et al., Nat. Biotech. 14:1246-1251 (1996), all of which are hereby incorporated by reference in their entirety). Included within the definition of GFP are derivatives of GFP, including amino acid substitutions, insertions and deletions. See for example WO 98/06737 and U.S. Pat. No. 5,777,079, both of which are hereby incorporated by reference in their entirety. Accordingly, the GFP proteins utilized in the present invention may be shorter or longer than the wild type sequence.

As used herein, a "disease" or "medical condition" is an abnormal condition of an organism that impairs bodily functions, associated with specific symptoms and signs.

As used herein, the term "cancer" refers to various types of malignant neoplasms, most of which can invade surrounding tissues, and may metastasize to different sites, as defined by Stedman's Medical Dictionary, 25th edition (Hensyl ed. 1990). Examples, without limitation, of cancers which may be treated using the compounds of the present invention include, but are not limited to, brain, ovarian, colon, prostate, kidney, bladder, breast, lung, oral, skin and blood cancers.

As used herein, a "tumor-seeking" group refers to an entity that is known to preferentially seek out and bind to surface structures on neoplastic cells that do not occur or are expressed to a substantially lesser degree by normal cells or entitles that preferentially accumulate in tumors over normal tissue.

As used herein, the terms "treat", "treating" and "treatment" refer to a method of alleviating or abrogating a disease and/or its attendant symptoms. The effect may be prophylactic in terms of completely or partially preventing a disorder or sign or symptom thereof, and/or may be therapeutic in terms of a partial or complete cure for a disorder and/or adverse effect attributable to the disorder. For example, the life expectancy of an individual affected with a cancer will be increased and/or that one or more of the symptoms of the disease will be reduced.

As used herein, "administer," "administering" or "administration" refers to the delivery of a compound or compounds of this invention or of a pharmaceutical composition containing a compound or compounds of this invention to a patient in a manner suitable for the treatment of a particular disease, such as cancer. "Administration" can be effected in one dose, continuously or intermittently throughout the course of treatment. Methods of determining the most effective means and dosage of administration are known to those of skill in the art and will vary with the composition used for therapy, the purpose of the therapy, the target cell being treated, and the subject being treated. Single or multiple administrations can be carried out with the dose level and pattern being selected by the treating physician. Suitable dosage formulations and methods of administering the agents are known in the art. Route of administration can also be determined and method of determining the most effective route of administration are known to those of skill in the art and will vary with the composition used for treatment, the purpose of the treatment, the health condition or disease stage of the subject being treated, and target cell or tissue. Non-limiting examples of route of administration include oral administration, nasal administration, injection, and topical application.

A "patient" or a "subject" refers to any higher organism that is susceptible to disease. Examples of such higher organisms include, without limitation, mice, rats, rabbits, dogs, cats, horses, cows, pigs, sheep, fish and reptiles. In some embodiments, "patient" or "subject" refers to a human being.

As used herein, the term "therapeutically effective amount" refers to that amount of a compound or combination of compounds of this invention which has the effect of (a) preventing a disorder from occurring in a subject that may be predisposed to a disorder, but may have not yet been diagnosed as having it; (b) inhibiting a disorder, i.e., arresting its development; or (c) relieving or ameliorating the disorder. For example, but not limited to, (1) reducing the size of the tumor; (2) inhibiting (that is, slowing to some extent, preferably stopping) tumor metastasis; (3) inhibiting to some extent (that is slowing to some extent, preferably stopping) tumor growth; (4) relieving to some extent (or preferably eliminating) one or more symptoms associated with the cancer; and/or (5) extending survival time of the patient.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

Methods and Compositions

From the viewpoint of structural biology and protein engineering, the members of the green fluorescent protein (GFP) family are exceptionally attractive objects. The tertiary structure of GFP is quite unique: it resembles a "cylinder" or a "β-barrel" that serves as a special container for an α-helix containing the covalently bonded chromophore. Although the central α-helix is located inside the β-barrel, it contains hydrophilic amino acids, and many molecules of bound water are present within the barrel interior. As the β-barrel is serving to protect the α-helix from the influence of the surroundings, a reasonable question arises whether it can function as a container for other peptides. It was hypothesized that the central α-helix of GFP can be substituted for foreign molecules, such as peptides. This possibility was explored by creating such a GFP-based system, where a toxic peptide is inserted into the β-barrel and thereby isolated from the environment (Example 1). To this end, the GFP modification was carried out by inserting an antimicrobial peptide into the central α-helix. The results of these experiments showed that such a chimeric protein is compact, soluble, and non-toxic for the production of molecules in cell culture. The data show that GFPs can be used as a container for storage and delivery of foreign peptides to cells both in vivo, ex vivo, and in vitro.

As described in Example 1, the peptide bactenecin was used as a substitute of the central α-helix in GFP. Bactenecin is a member of the group of antimicrobial peptides. It is synthesized by neutrophils and has an activity against Gram-negative bacteria, such as *Escherichia coli, Pseudomonas aeruginosa*, and *Salmonella typhimurium* (Wu 1999). The selection was based on the length and position of hydrophilic and hydrophobic amino acids within the bactenecin amino acid sequence.

Figure 1A:
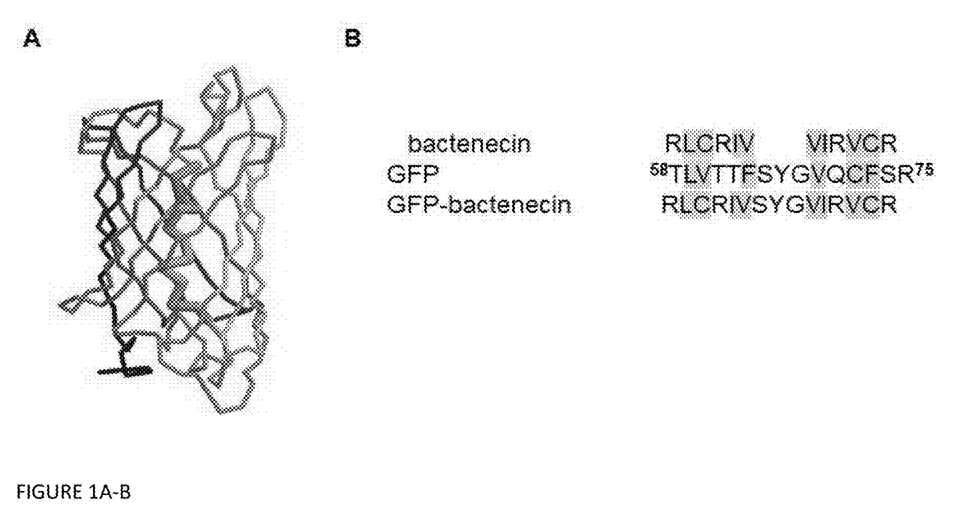

Therefore, disclosed herein is a composition comprising a modified green fluorescent protein (GFP) molecule and a non-native molecule, wherein the non-native molecule is embedded within the modified GFP molecule (See FIG. 1A). One or more amino acids within the modified GFP molecule can be modified in order to confer stability to composition. For example, or more modified amino acids can comprise one or more amino acid substitutions, such as hydrophobic amino acids. The one or more amino acid substitutions can comprise at least one of F8D, Q177E, or I167D in native GFP. A modified GFP molecule can comprise one, two, or all three of these mutations, or a combination of these three. The modified GFP can comprise other mutations that confer desired characteristics to the molecule. Native GFP is represented in SEQ ID NO: 2, and all three substitutions are found in SEQ ID NO: 4.

Further disclosed is a method for treating a subject in need thereof, the method comprising administering to the subject a composition comprising a modified GFP molecule and a non-native molecule, wherein the non-native molecule is embedded within the modified GFP molecule, and further wherein the non-native molecule is useful in treating the subject. One or more of the amino acids within the modified GFP molecule can be modified in order to confer stability to composition. The modified GFP molecule can be capable of fluorescence, thereby enabling simultaneous detection and treatment.

Disclosed herein is a method for delivering a desired molecule to a cell, the method comprising exposing a cell to a composition comprising a modified GFP molecule and a non-native molecule, wherein the non-native molecule is embedded within the modified GFP molecule. In some embodiments, the modified GFP molecule can be targeted to the cell. This method is applicable both in vitro and in vivo. When used in vitro, GFP can be used to deliver cargo to a certain cell for analysis. In one example, the GFP modified with the cargo can be expressed by the cell itself.

The non-native molecule can be a therapeutic, diagnostic, or prophylactic molecule. For example, the non-native molecule can comprise one or more of an antineoplastic agent, an immunomodulating agent, a neuroactive agent, an anti-inflammatory agent, an antilipidemic agent, a hormone, a receptor agonist or antagonist, or an anti-infective agent, or a compound selected from a protein, a peptide, an antibody, an enzyme, a hormone, a cofactor, a steroid, a detection agent, an imaging agent, a contrast agent, a gas, a pharmaceutically-active molecule, or a combination thereof. The modified GFP molecule can be capable of fluorescence.

More specifically, the present invention can provide methods for delivering therapeutic agents to subjects in need thereof. Such therapeutic agents can comprise, but are not limited to, antivirals, antimicrobials, chemotherapeutics, and any other drug or prodrug. Additional embodiments of the present invention provide compositions and methods for targeting and delivering many other therapeutic molecule including, but not limited to: agents that induce apoptosis (e.g., Geranylgeraniol [3,7,11,15-tetramethyl-2,6,10,14-hexadecatraen-1-ol], pro-apoptotic Bcl-2 family proteins including Bax, Bak, Bid, and Bad); polynucleotides (e.g., DNA, RNA, ribozymes, RNAse, siRNAs, etc); polypeptides (e.g., enzymes); photodynamic compounds (e.g., Photofrin (II), ruthenium red compounds [e.g., Ru-diphenyl-phenanthroline and Tris(1-10-phenanthroline) ruthenium (II) chloride], tin ethyl etiopurpurin, protoporphyrin IX, chloroaluminum phthalocyanine, tetra(M-hydroxyphenyl) chlorin)); radiodynamic (i.e., scintillating) compounds (e.g., NaI-125, 2,5-diphenyloxazole (PPO); 2-(4-biphenyl)-6-phenylbenzoxazole; 2,5-bis-(5'-tert-butylbenzoxazoyl-[2'])thiophene; 2-(4-t-butylphenyl)-5-(4-biphenylyl)-1,3,4-oxadiazole; 1,6-diphenyl-1,3,5-hexatriene; trans-p,p'-diphenylstilbene; 2-(1-naphthyl)-5-phenyloxazole; 2-phenyl-5-(4-biphenylyl)-1,3,4-oxadiazole; p-terphenyl; and 1,1,4,4-tetraphenyl-1,3-butadiene); radioactive elements or compounds that emits gamma rays (e.g., $^{111}$In-oxine, $^{59}$Fe, $^{67}$Cu, $^{125}$I, $^{99}$Te (Technetium), and $^{14}$Cr); radioactive elements or compounds that emit beta particles (e.g., $^{32}$P, $^{3}$H, $^{35}$S, $^{14}$C); drugs; biological mimetics; alkaloids; alkylating agents; antitumor antibiotics; antimetabolites; hormones; platinum compounds; monoclonal antibodies conjugated to anticancer drugs, toxins and/or defensins, radionuclides; biological response modifiers (e.g., interferons [e.g., IFN-α, etc], and interleukins [e.g., IL-2]); adoptive immunotherapy agents; hematopoietic growth factors; agents that induce tumor cell differentiation (e.g., all-trans-retinoic acid, etc); gene therapy reagents (e.g., antisense therapy reagents and nucleotides); tumor vaccines; and angiogenesis inhibitors and the like. Those skilled in the art are aware of numerous additional drugs and therapeutic agents suitable for delivery by the compositions of the present invention.

In preferred embodiments, the anticancer agents carried by the modified GFP component comprise agents that induce or stimulate apoptosis including, but not limited to: kinase inhibitors (e.g., epidermal growth factor receptor kinase inhibitor [EGFR]); vascular growth factor receptor kinase inhibitor [VGFR]; fibroblast growth factor receptor kinase inhibitor [FGFR]; platelet-derived growth factor receptor kinase inhibitor [PGFR]; and Bcr-Abl kinase inhibitors such as STI-571, GLEEVEC, and GLIVEC); antisense molecules; antibodies (e.g., HERCEPTIN and RITUXAN); anti-estrogens (e.g., RALOXIFENE and TAMOXIFEN); anti-androgens (e.g., flutamide, bicalutamide, finasteride, aminoglutethamide, ketoconazole, and corticosteroids); cyclooxygenase 2 (COX-2) inhibitors (e.g., Celecoxib, Meloxicam, NS-398); non-steroidal anti-inflammatory drugs (NSAIDs); and chemotherapeutic drugs (e.g., irinotecan [Camptosar], CPT-11, fludarabine [Fludara], dacarbazine [DTIC], dexamethasone, mitoxantrone, Mylotarg, VP-16, cisplatinum, 5-FU, Doxrubicin, Taxotere or taxol); cellular signaling molecules; ceramides and cytokines; and staurosprine and the like.

In some preferred embodiments, various compositions of the present invention provide treatments for a number of conditions including, but not limited to, breast cancer, prostate cancer, lung cancer, lymphomas, skin cancer, pancreatic cancer, colon cancer, melanoma, ovarian cancer, brain cancer, head and neck cancer, liver cancer, bladder cancer, non-small lung cancer, cervical carcinoma, leukemia, neuroblastoma and glioblastoma, and T and B cell mediated autoimmune diseases and the like.

In some preferred embodiments, the modified GFP compositions of the present invention are optimized to target and deliver to cancer cells anticancer drugs/agents including, but not limited to: altretamine; asparaginase; bleomycin; capecitabine; carboplatin; carmustine; BCNU; cladribine; cisplatin; cyclophosphamide; cytarabine; dacarbazine; dactinomycin; actinomycin D; Docetaxel; doxorubicin; imatinib; etoposide; VP-16; fludarabine; fluorouracil; 5-FU; gemcitabine; hydroxyurea; idarubicin; ifosfamide; irinotecan; CPT-11; methotrexate; mitomycin; mitomycin-C; mitotane; mitoxantrone; paclitaxel; topotecan; vinblastine; vincristine; and vinorelbine.

In still other embodiments, the targeted cells or tissues are cancer cells selected from topical cells (e.g., malignant melanoma cells and basal cell carcinomas), ductal cells (e.g., mammary ductal adenocarcinoma cell and bowel cancer cells), and deep tissue cells (e.g., hepatocellular carcinoma cells, CNS primary lymphoma cells, and glioma cells).

In some preferred embodiments, the modified GFP compositions of the present invention are optimized to target and deliver antiretroviral drugs and/or agents to cells that inhibit the growth and replication of the human immunodeficiency virus (HIV). Exemplary drugs and agents in this regard include, but are not limited to: nucleotide analogue reverse transcriptase inhibitors (e.g., tenofovir disoproxil fumarate [DF]); nucleoside analogue reverse transcriptase inhibitors (NRTIs) (e.g., zidovudine, lamivudine, abacavir, zalcitabine, didanosine, stavudine, zidovudine+lamivudine, and abacavir+zidovudine+lamivudine); non-nucleoside reverse transcriptase inhibitors (NNRTIs) (e.g., nevirapine, delavirdine, and efavirenz); protease inhibitors (PIs) (e.g., saquinavir [SQV (HGC)], saquinavir [SQV (SGC)], ritonavir, indinavir, nelfinavir, amprenavir, and lopinavir+ritonavir); and combinations thereof (e.g., highly active anti-retroviral therapy [HAART]).

In still other embodiments, the modified GFP compositions of the present invention are optimized to target and deliver drugs and other therapeutic agents to cells for the treatment of diabetes (e.g., types I and II) or the symptoms that commonly arise from this disease. In this regard, certain embodiments of the present invention target and deliver the following exemplary diabetes treatments: insulin (e.g., rapid acting insulin [e.g., insulin lispro]; short acting insulin [e.g., insulin regular]; intermediate acting [e.g., insulin isophane]; long acting insulin [e.g., insulin zinc extended]; very long acting insulin [e.g., insulin glargine]); sulfonylureas (e.g., first generation sulfonylureas [e.g., acetohexamide, chlorpropamide, tolazamide, and tolbutamide]; second generation sulfonylureas [e.g., glimepiride, gipizide, glyburide]); biguanides (e.g., metformin); sulfonylurea/biguanide combination; α-glucosidase inhibitors (e.g., acarabose, and miglitol); thiazolidinediones (glitazones) (e.g., pioglitazone, rosiglitazone); and meglitinides (e.g., repaglinide, nateglinide).

In other embodiments, the modified GFP compositions of the present invention are optimized to target and deliver to cells drugs and other therapeutic agents for the treatment of psychological health issues including, but not limited to, depression (e.g., minor and depressive illness). Depression is the most common mental health problem in the US. While the exact cause of depression remains unknown, depression is thought to caused by a malfunction of brain neurotransmitters. Antidepressants are often prescribed to treat depressive illnesses. The most common prescribed type of antidepressants are the selective serotonin reuptake inhibitors (SSRIs) (e.g., PROZAC (Fluoxetine hydrochloride), PAXIL (paroxetine hydrochloride), ZOLOFT (sertraline hydrochloride), CELEXA (citalopram HBr), SERZONE (nefazodone), REMERON (mitrazapine), and EFFEXOR (venlafaxine HCl)).

In some embodiments, the biological includes a target epitope. The range of target epitopes is practically unlimited. Indeed, any inter- or intra-biological feature (e.g., glycoprotein) of a cell or tissue is encompassed within the present invention. For example, in some embodiments, target epitopes are selected from cell surface proteins, cell surface receptors, cell surface polysaccharides, extracellular matrix proteins, a viral coat protein, a bacterial cell wall protein, a viral or bacterial polysaccharide, intracellular proteins, and intracellular nucleic acids. In still other embodiments, the modified GFP composition is targeted via a signal peptide to a particular cellular organelle (e.g., mitochondria or the nucleus).

In some embodiments, the modified GFP compositions of the present invention are used to treat (e.g., mediate the translocation of drugs and/or prodrugs into) diseased cells and tissues. In this regard, various diseases are amenable to treatment using the present modified GFP compositions and methods. An exemplary list of diseases includes: breast cancer; prostate cancer; lung cancer; lymphomas; skin cancer; pancreatic cancer; colon cancer; melanoma; ovarian cancer; brain cancer; head and neck cancer; liver cancer; bladder cancer; non-small lung cancer; cervical carcinoma; leukemia; neuroblastoma and glioblastoma; T and B cell mediated autoimmune diseases; inflammatory diseases; infections; hyperproliferative diseases; AIDS; degenerative conditions, vascular diseases, and the like. In some embodiments, the treated cancer cells are metastatic.

Still other specific compositions and methods are directed to treating cancer in a subject comprising: administering to a patient having cancer, wherein the cancer is characterized by resistance to cancer therapies (e.g., chemoresistant, radiation resistant, hormone resistant, and the like), an effective amount an anticancer drug or prodrug.

In some embodiments, the present invention provides modified GFP compositions and methods suitable for treating infections or for destroying infectious agents. In this regard, the present invention provides embodiments for treating infections caused by viruses, bacteria, fungi, mycoplasma, and the like. The present invention in not limited, however, to treating any particular infection or to the destruction of any particular infectious agent. For example, in some embodiments, the present invention provides compositions directed to treating (e.g., mediating the translocation of a therapeutic agents) to ameliorate diseases caused by the following exemplary pathogens: *Bartonella henselae, Borrelia burgdorferi, Campylobacter jejuni, Campylobacter fetus, Chlamydia trachomatis, Chlamydia pneumoniae, Chylamydia psittaci, Simkania negevensis, Escherichia coli* (e.g., 0 1 57: H7 and K88), *Ehrlichia chafeensis, Clostridium botulinum, Clostridium perfringens, Clostridium tetani, Enterococcusfaecalis, Haemophilus influenzae, Haemophilus ducreyi, Coccidioides immitis, Bordetella pertussis, Coxiella burnetii, Ureaplasma urealyticum, Mycoplasma genitalium, Trichomatis vaginalis, Helicobacterpylori, Helicobacter hepaticus, Legionella pneumophila, Mycobacterium tuberculosis, Mycobacterium bovis, Mycobacterium africanum, Mycobacterium leprae, Mycobacterium asiaticum, Mycobacterium avium, Mycobacterium celatum, Mycobacterium celonae, Mycobacteriumfortuitum, Mycobacterium genavense, Mycobacterium haemophilu Mycobacterium intracellulare, Mycobacterium kansasii, Mycobacterium malmoense, Mycobacterium marinum, Mycobacterium scrofulaceum, Mycobacterium simiae, Mycobacterium szulgai, Mycobacterium ulcerans, Mycobacterium xenopi, Corynebacterium diptheriae, Rhodococcus equi, Rickettsia aeschlimannii, Rickettsia africae, Rickettsia conorii, Arcanobacterium haemolyticum, Bacillus anthracis, Bacillus cereus, Lysteria monocytogenes, Yersinia pestis, Yersinia enterocolitica, Shigella dysenteriae, Neisseria meningitides, Neisseria gonorrhoeae, Streptococcus bovis, Streptococcus hemolyticus, Streptococcus mutans, Streptococcus pyogenes, Streptococcus pneumoniae, Staphylococcus aureus, Staphylococcus epidermidis, Staphylococcus pneumoniae, Staphylococcus saprophyticus, Vibrio cholerae, Vibrio parahaemolyticus, Salmonella typhi, Salmonella paratyphi, Salmonella enteritidis, Treponema pallidum,* Human rhinovirus, Human coronavirus, Dengue virus, Filoviruses (e.g., Marburg and Ebola viruses), Hantavirus, Rift Valley virus, Hepatitis B, C, and E, Human Immunodeficiency Virus (e.g., HIV-1, HIV-2), HHV-8, Human papillomavirus, Herpes virus (e.g., HV-I and HV-II), Human T-cell lymphotrophic viruses (e.g., HTLV-I and HTLV-II), Bovine leukemia virus, Influenza virus, Guanarito virus, Lassa virus, Measles virus, Rubella virus, Mumps virus, Chickenpox (Varicella virus), Monkey pox, Epstein Bahr virus, Norwalk (and Norwalk-like) viruses, Rotavirus, Parvovirus B19, Hantaan virus, Sin Nombre virus, Venezuelan equine encephalitis, Sabia virus, West Nile virus, Yellow Fever virus, causative agents of transmissible spongiform encephalopathies, Creutzfeldt-Jakob disease agent, variant Creutzfeldt-Jakob disease agent, *Candida, Ccryptoccus, Cryptosporidium, Giardia lamblia, Microsporidia, Plasmodium vivax, Pneumocystis carinii, Toxoplasma gondii, Trichophyton mentagrophytes, Enterocytozoon bieneusi, Cyclospora cayetanensis, Encephalitozoon hellem, Encephalitozoon cuniculi,* among other viruses, bacteria, archaea, protozoa, fungi and the like).

Some other embodiments the present invention provides pharmaceutical compositions comprising: a modified GFP composition as described herein; and/or instructions for administering the modified GFP composition to a subject, the subject characterized as having a disease state.

Other preferred embodiments of the compositions of the present invention comprise a cellular recognition element. The present invention contemplates that the cellular recognition elements interact (e.g., bind) to a biological targets. In some embodiments, the molecular recognition elements comprise at least a portion of an antibody, nucleic acid, or peptide signal sequence, and the like.

Contemplated biological targets include, but are not limited to, cell surface proteins, cell surface receptors, cell surface polysaccharides, extracellular matrix proteins, intracellular proteins and intracellular nucleic acids, and the like.

In particularly preferred embodiments, the biological target is on the surface of a diseased cell (e.g., a diseased neuronal cell). In some of these embodiments, the diseased neuronal cell is afflicted with a neurodegenerative disease (e.g., Parkinson's disease). In other embodiments, the diseased cell comprises a cancer cell.

In still other embodiments, the modified GFP compositions of the present invention are optimized to target and deliver drugs and other therapeutic agents to cells for the treatment of diabetes (e.g., types I and II) or the symptoms that commonly arise from this disease. In this regard, certain embodiments of the present invention target and deliver the following exemplary diabetes treatments: insulin (e.g., rapid acting insulin [e.g., insulin lispro]; short acting insulin [e.g., insulin regular]; intermediate acting [e.g., insulin isophane]; long acting insulin [e.g., insulin zinc extended]; very long acting insulin [e.g., insulin glargine]); sulfonylureas (e.g., first generation sulfonylureas [e.g., acetohexamide, chlorpropamide, tolazamide, and tolbutamide]; second generation sulfonylureas [e.g., glimepiride, gipizide, glyburide]); biguanides (e.g., metformin); sulfonylurea/biguanide combination; α-glucosidase inhibitors (e.g., acarabose, and miglitol); thiazolidinediones (glitazones) (e.g., pioglitazone, rosiglitazone); and meglitinides (e.g., repaglinide, nateglinide).

In other embodiments, the modified GFP compositions of the present invention are optimized to target and deliver to cells drugs and other therapeutic agents for the treatment of psychological health issues including, but not limited to, depression (e.g., minor and depressive illness). Depression is the most common mental health problem in the US. While the exact cause of depression remains unknown, depression is thought to be caused by a malfunction of brain neurotransmitters. Antidepressants are often prescribed to treat depressive illnesses. The most common prescribed type of antidepressants are the selective serotonin reuptake inhibitors (SSRIs) (e.g., PROZAC (Fluoxetine hydrochloride), PAXIL (paroxetine hydrochloride), ZOLOFT (sertraline hydrochloride), CELEXA (citalopram HBr), SERZONE (nefazodone), REMERON (mitrazapine), and EFFEXOR (venlafaxine HCl)).

In some embodiments, the biological target includes a target epitope. The range of target epitopes is practically unlimited. Indeed, any inter- or intra-biological feature (e.g., glycoprotein) of a cell or tissue is encompassed within the present invention. For example, in some embodiments, target epitopes are selected from cell surface proteins, cell surface receptors, cell surface polysaccharides, extracellular matrix proteins, a viral coat protein, a bacterial cell wall protein, a viral or bacterial polysaccharide, intracellular proteins, and intracellular nucleic acids. In still other embodiments, the modified GFP composition is targeted via a signal peptide to a particular cellular organelle (e.g., mitochondria or the nucleus).

In certain embodiments, the compositions of the present invention are used for simultaneous tumor imaging and drug therapy. Some other embodiments the present invention provide pharmaceutical compositions comprising: a modified GFP composition as described herein; and/or instructions for administering the modified GFP composition to a subject, the subject characterized as having a disease state (e.g., cancer).

The GFP molecule itself can be used as an imaging agent, in either in vivo, ex vivo, or in vitro applications. There are many uses for GFP known to those of skill in the art, and the methods disclosed herein can allow for the simultaneous delivery of cargo, as well as imaging, of certain cells. Methods for imaging GFP are known in the art. For example Hoffman (Application of GFP imaging in cancer. Lab Invest. 2015; 95 (4): 432-452. doi: 10.1038/labinvest.2014.154) discloses methods of in vivo imaging GFP in cancer diagnostics. Disclosed herein are methods for imaging and treating simultaneously.

A wide array of GFP-based fluorescent biosensors has been designed to detect a variety of intracellular conditions, including ion (such as Ca2+) concentrations and pH, using a range of strategies such as FRET, calmodulin, and others. It can also be used as a biosensor, in optogenetics, (to detect, measure, and control molecular signals, cells, and groups of cells), cell marking/selection (which can serve as an alternative to antibiotic selection). Plasmids of this type may have the GFP under the control of an additional promoter from that of the gene of interest, or expressed from the same transcript as the gene of interest, but after an internal ribosome entry site (IRES). This is oftentimes used in conjunction with FACS (see below). GFP can also be used with fluorescence-activated cell sorting (FACS). This is a type of flow cytometry that separates mixtures of cells into distinct populations based on fluorescent signal. Thus, FACS can be used to separate cells expressing GFP from cells that are not, and with the instant invention, a cargo can be simultaneously delivered.

GFP can also be used in developmental/transgenic uses. Because of its stability, GFP can be used in lineage tracking capacities in cell fate studies. It can also be used, when put under control of promoters of interest, to visualize the developmental stage at which these promoters are active. Further, GFP can label transgenically modified ES cells, which can then be used for implantation and generation of transgenic mice.

Purification: GFP can be used as a general epitope tag for protein purification and a number of commercial antibodies to GFP are available.

Also disclosed is a nucleic acid encoding a modified GFP molecule and a non-native peptide, wherein said non-native peptide is within the central α-helical moiety of GFP. At least a part of the α-helical moiety of naturally occurring GFP is replaced with a non-native peptide. Also disclosed is a cell stably transformed with a nucleic acid encoding the modified GFP comprising a foreign peptide. One may express the modified GFP disclosed herein in recombinantly engineered cells such as bacteria, yeast, insect, mammalian, or plant cells. It is expected that those of skill in the art are knowledgeable in the numerous expression systems available for expression of a nucleic acid encoding a protein of the present invention.

In brief summary, the expression of isolated nucleic acids encoding the modified GFP of the present invention will typically be achieved by operably linking, for example, the DNA or cDNA to a promoter (which is either constitutive or regulatable), followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding a protein of the present invention. Either prokaryotic or eukaryotic cells can be transformed to stably express the modified GFPs disclosed herein.

There are a number of suitable host cell lines capable of expressing intact proteins that have been developed in the art, and include the HEK293, BHK21, and CHO cell lines, for example. Expression vectors for these cells can include expression control sequences, such as an origin of replication, a promoter (e.g., the CMV promoter, a HSV tk promoter or pgk (phosphoglycerate kinase) promoter), an enhancer, and necessary processing information sites, such as ribosome binding sites, RNA splice sites, polyadenylation sites (e.g., an SV40 large T Ag poly A addition site), and transcriptional terminator sequences. Other animal cells useful for production of proteins of the present invention are available, for instance, from the American Type Culture Collection Catalogue of Cell Lines and Hybridomas (7th edition, 1992).

The method of transformation/transfection is not critical to the instant invention; various methods of transformation or transfection are currently available. As newer methods are available to host cells they may be directly applied. Accordingly, a wide variety of methods have been developed to insert a DNA sequence into the genome of a host cell to obtain the transcription and/or translation of the sequence to effect phenotypic changes in the organism. Thus, any method which provides for efficient transformation/transfection may be employed.

EXAMPLES

To further illustrate the principles of the present disclosure, the following examples are put forth so as to provide those of ordinary skill in the art with a complete disclosure and description of how the compositions, articles, and methods claimed herein are made and evaluated. They are intended to be purely exemplary of the invention and are not intended to limit the scope of what the inventors regard as their disclosure. Efforts have been made to ensure accuracy with respect to numbers (e.g., amounts, temperatures, etc.); however, some errors and deviations should be accounted for. Unless indicated otherwise, temperature is ° C. or is at ambient temperature, and pressure is at or near atmospheric. There are numerous variations and combinations of process conditions that can be used to optimize product quality and performance. Only reasonable and routine experimentation will be required to optimize such process conditions.

Example 1: Natural Container for Drug Storage and Delivery: Chimeric GFP with Embedded Foreign Peptide Materials and Methods Hybrid protein design was carried out using the RasMol program. Optimization of hybrid protein was carried out by molecular dynamics method in Gromacs 4.5.3 program (Abraham 2015) using the CHARMM27 force field. Spatial structure of GFP (1B9C, (Battistutta 2000), from Protein data bank, PDB: was used as a starting model for molecular dynamics. The model was placed into 65×65×65 Å orthorhombic water box filled with TIP3P water molecules. The water box was built so that the distance from the protein surface in each direction to the edge of water box was at least 12 Å. To test the quality of the obtained structures, deviations of stereo-chemical parameters after 270 ns molecular dynamics were calculated. No significant deviation of protein coordinates from starting conformation was observed, indicating that the structure of GFP fluctuated around its equilibrium position. Root-mean square deviations for all the atoms of the system did not exceed 3 Å (2 Å for Cα atoms of proteins) in all the trajectories. To analyze the effect of mutations on protein structure, 300 ns molecular dynamics trajectories were simulated at constant temperature, 300K and pressure, 1 atm. All the simulations were carried out using computational resources of Joint SuperComputer Center of the Russian Academy of Sciences (JSCC RAS). The coordinates of the system were saved and analyzed every 1 ps.

DNA synthesis and protein isolation. DNA fragment encoding the hybrid protein GFP-bactenicin was synthesized by PCR with overlapping primers. cDNA fragment was cloned in expression vector pET28a using NdeI and EcoRI restriction sites. Site-directed mutagenesis was carried out as described earlier (Glukhova 2017; Melnik 2012).

Recombinant proteins were produced in cell cultures of $E.$ $coli$ BL21 (DE3). Protein synthesis was induced by addition of isopropyl-β-D-1-thiogalactoside (IPTG) to the final concentration of 0.1 mM at OD600=0.5. The cells were cultivated for 16 h at 18° C. Cell pellet was resuspended in 20 mM Tris-HCl buffer, pH 8.0, supplied with 1 mM EDTA, and disrupted by an ultrasonic disintegrator Branson Sonifier. Cell lysates were centrifuged at 20 000 g for 30 min. Supernatant and pellet were analyzed by PAAG electrophoresis in denaturing conditions.

Computational analysis of intrinsic disorder predisposition. The effects of the bactenecin insertion and the F8D, I167D, and Q177E mutations on the intrinsic disorder predisposition of GFP using a set of commonly utilized per-residue disorder predictors, which were selected based on their specific features: PONDR® VLXT is sensitive to local sequence peculiarities (Li 1999; Romero 2001) PONDR® VL3 shows high accuracy in prediction of long disordered regions (Peng 2005) PONDR® VSL2 is a rather accurate predictor of both short and long disordered regions (Obradovic 2005; Peng 2006). PONDR® FIT is a meta-predictor combining outputs of six individual disorder predictors and showing noticeably improved prediction accuracy compared to the accuracy of its component predictors (Xue 2010) and IUPred provides evaluations of short and long disordered regions (Dosztanvi 2005; Meszaros 2018).

Results and Discussion

A hybrid protein, GFP-bactenecin, with a part of the central α-helical moiety of GFP being substituted for bactenecin amino acids, was constructed. Three amino acids, S, Y, and G, which form a unique chromophore in the native GFP, were embedded into the bactenecin. FIG. 1 shows the structure of GFP and the amino acid sequences of bactenecin, natural central α-helix GFP, and hybrid GFP-bactenecin sequence.

Figure 2:
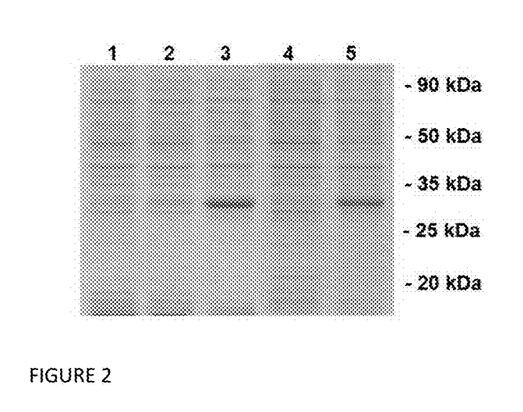

Very similar arrangement and alternation of hydrophilic and hydrophobic amino acids specific for α-helices of soluble proteins are observed in the amino acid sequences of bactenecin (SEQ ID NO: 1) and the central α-helix of GFP (FIG. 1B) (SEQ ID NO: 2). Nevertheless, the designed insertion of bactenecin instead of the central α-helix alters the majority of amino acid residues in the center of GFP (FIG. 1, SEQ ID NO: 3). Therefore, the first task was to analyze the capability of GFP to fold after multiple substitutions within its central α-helix. To this end, the hybrid protein was produced in $E.$ $coli$ bacterial culture. It was found that GFP-bactenecin is synthesized in a significant amount, and it is not toxic for the culture of producer. However, the cells had no characteristic green fluorescence, indicating that the chromophore was not properly formed in the hybrid protein. After ultrasound disintegration of producer cells, GFP-bactenecin hybrid was detected in insoluble protein fraction (FIG. 2). This observation is the evidence that GFP-bactenecin is unstable and forms aggregates, thereby indicating that the modifications introduced into the central α-helix lead to the misfolding and aggregation of GFP.

Figure 3A:
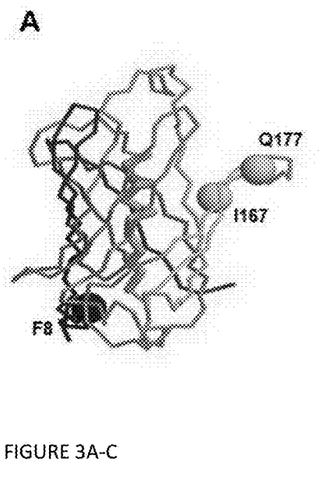
FIG. 3A-C shows (A) Modeled structure of GFP-bactenicin. (B) Optimized structure of GFP-bactenecin protein with stabilizing mutations F8D, I167D, and Q177E. (C) Electrophoregram of the cell samples producing optimized GFP-bactenecin after 4 h of induction by IPTG, where;
1—soluble protein fraction,
2—insoluble protein fraction.
Figure 3B:
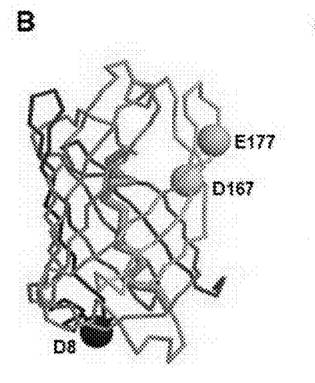

As wild-type GFP is strongly aggregating at elevated temperature or in presence of denaturants (Tsien 1998; Stepanenko 2013), it was hypothesized that the reason for the aggregation of chimeric protein could be destabilization of the protein structure. To search for mutations capable of stabilizing the GFP-bactenecin chimera, improving its folding and thus decreasing aggregation, modeling of GFP structure by molecular dynamics was carried out. The analysis of GFP-bactenecin structure by molecular dynamics and its comparison with the structure of wild-type protein showed that substitutions of three amino acids (F8D, I167D, Q177E) could actually stabilize this protein, since simulation of the modeled protein with F8D, I167D, Q177E substitutions showed that the chosen mutations improve the compactness of the protein and possibly stabilize it. FIG. 3 shows the structure of GFP-bactenecin protein (FIG. 3A) simulated by molecular dynamics method and structure of GFP-bactenecin protein with additional stabilizing mutations F8D, I167D, and Q177E (FIG. 3B). It can be seen that the structure of GFP-bactenecin is «distorted» compared to wild-type protein. Simulation of GFP-bactenecin with additional mutations showed that the chosen mutations could stabilize protein structure.

Figure 4A:
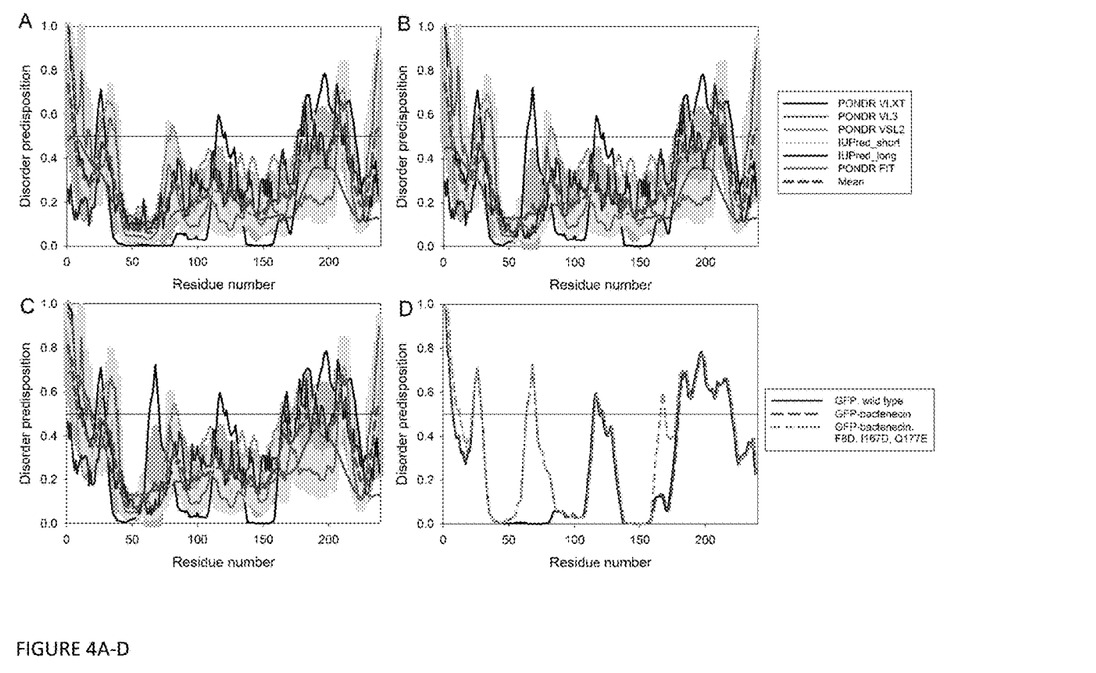

Next, the effects of the bactenecin insertion and the F8D, I167D, and Q177E mutations on the intrinsic disorder predisposition of GFP was analyzed using a set of commonly utilized per-residue disorder predictors. Results of these analyses are shown in FIG. 4. It is seen that these mutations affected disorder predisposition of GFP, with the strongest effect being from the introduction of bactenecin. Although the outputs of all tools used for the disorder prediction reflected these changes, most noticeable changes were detected by PONDR® VLXT, which is not surprising since this predictor is very sensitive to the local amino acid sequence peculiarities. Therefore, the results generated by this predictor are presented in FIG. 4D, which shows that the insertion of the bactenecin sequence instead of native central α-helix causes appearance of a new disordered region. This increased propensity for intrinsic disorder can be the reason for the distorted structure of the GFP-bactenicin (see FIG. 3A). FIG. 4D also provides an explanation for the structure-stabilizing effects of the F8D, I167D, and Q177E mutations. Since regions surrounding these sites are predicted to be ordered (especially in the vicinity of 1167), it can be that their local rigidity precludes GFP-bactenicin from structural adjustment. Increased local disorder introduced by the F8D, I167D, and Q177E mutations provides this protein with enough structural flexibility to promote formation of more compact structure (see FIG. 3B).

Figure 3C:
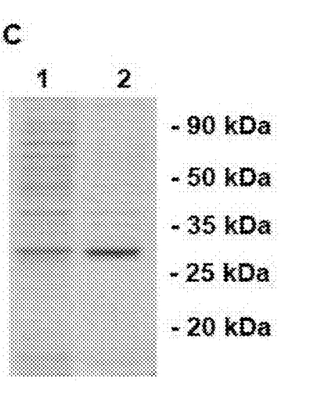

As a result of these manipulations, an optimized GFP-bactenecin variant with stabilizing F8D, I167D, Q177E substitutions was constructed. The optimized protein had no toxic effect on the cells during its production in bacterial culture. Unlike the original GFP-bactenecin variant, part of the optimized protein was detected in soluble protein fraction after ultrasound disintegration of the cells (FIG. 3C). Therefore, the inserted substitutions stabilized the protein structure and reduced aggregation.

Data reported in this study show that GFP can be used as a container for peptides. The results of this and earlier work (Glukhova 2017), as well as the outputs of the molecular dynamics-based computational analysis, show that although the substitution of a large number of hydrophilic or hydrophobic amino acids within the central α-helix destabilizes GFP, this protein is not precluded from the formation of a structure similar to that of the wild-type protein.

It will be apparent to those skilled in the art that various modifications and variations can be made in the present disclosure without departing from the scope or spirit of the invention. Other embodiments of the disclosure will be apparent to those skilled in the art from consideration of the specification and practice of the methods disclosed herein. It is intended that the specification and examples be considered as exemplary only, with a true scope and spirit of the invention being indicated by the following claims.

```
SEQUENCES
SEQ ID NO: 1: bactinecin
RLCRIVSYGVIRVCRR

SEQ ID NO: 2: Green fluorescent protein OS =
Aequorea victoria
MSKGEELFTGVVPILVELDGDVNGHKFSVSGEGEGDATYGKLTLKFICT
TGKLPVPWPTLVTTFSYGVQCFSRYPDHMKQHDFFKSAMPEGYVQERTI
FFKDDGNYKTRAEVKFEGDTLVNRIELKGIDFKEDGNILGHKLEYNYNS
HNVYIMADKQKNGIKVNFKIRHNIEDGSVQLADHYQQNTPIGDGPVLLP
DNHYLSTQSALSKDPNEKRDHMVLLEFVTAAGITHGMDELYK SEQ ID NO: 3: Green fluorescent protein with
bactinecin OS = Aequorea victoria
MSKGEELITGVVPILVELDGDVNGHKFSVSGEGEGDATYGKLTLKFICT
TGKLPVPWPRLCRIVSYGVIRVCRRYPDHMKQHDFFKSAMPEGYVQERT
IFFKDDGNYKTRAEVKFEGDTLVNRIELKGIDFKEDGNILGHKLEYNYN
SHNVYIMADKQKNGIKVNFKIRHNIEDGSVQLADHYQQNTPIGDGPVLL
PDNHYLSTQSALSKDPNEKRDHMVLLEFVTAAGITHGMDELYK SEQ ID NO: 4: GFP with F8D, I167D, Q177E mutations
MSKGEELDTGVVPILVELDGDVNGHKFSVSGEGEGDATYGKLTLKFICT
TGKLPVPWPTLVTTFSYGVQCFSRYPDHMKQHDFFKSAMPEGYVQERTI
FFKDDGNYKTRAEVKFEGDTLVNRIELKGIDFKEDGNILGHKLEYNYNS
HNVYIMADKQKNGIKVNFKDRHNIEDGSVELADHYQQNTPIGDGPVLLP
DNHYLSTQSALSKDPNEKRDHMVLLEFVTAAGITHGMDELYK SEQ ID NO: 5 Green fluorescent protein with
bactinecin and F8D, I167D, Q177E mutations
MSKGEELDTGVVPILVELDGDVNGHKFSVSGEGEGDATYGKLTLKFICT
TGKLPVPWPRLCRIVSYGVIRVCRRYPDHMKQHDFFKSAMPEGYVQERT
IFFKDDGNYKTRAEVKFEGDTLVNRIELKGIDFKEDGNILGHKLEYNYN
SHNVYIMADKQKNGIKVNFKDRHNIEDGSVELADHYQQNTPIGDGPVLL
PDNHYLSTQSALSKDPNEKRDHMVLLEFVTAAGITHGMDELYK
```

REFERENCES

1. Hancock R. E., Haney E. F., Gill E. E. The immunology of host defence peptides: beyond antimicrobial activity. Nat Rev Immunol, 2016, vol. 16, pp. 321-334. doi: 10.1038/nri.2016.29.
2. Li Y. Carrier proteins for fusion expression of antimicrobial peptides in *Escherichia coli* Biotechnol. Appl. Biochem, 2009, vol. 54, pp. 1-9. doi: 10.1042/BA20090087.
3. Urbán P., Valle-Delgado J. J., Moles E., Marques J., Díez C., Fernandez-Busquets X. Nanotools for the delivery of antimicrobial peptides. Curr Drug Targets, 2012, vol. 13, pp. 1158-1172. doi: 10.2174/138945012802002302.
4. Bokman S. H., Ward W. W. Renaturation of Aequorea green-fluorescent protein. Biochem Biophys Res Commun, 1981, vol. 101, pp. 1372-1380. doi: 10.1016/0006-291X (81) 91599-0
5. Ormö M., Cubitt A. B., Kallio K., Gross L. A., Tsien R. Y., Remington S. J. Crystal structure of the *Aequorea victoria* green fluorescent protein. Science, 1996, vol. 273, pp. 1392-1395. doi: 0.1126/science.273.5280.1392.
6. Glukhova K. F., Marchenkov V. V., Melnik T. N., Melnik B. S. Isoforms of green fluorescent protein differ from each other in solvent molecules 'trapped' inside this protein. J Biomol Struct Dyn, 2017, vol. 35, pp. 1215-1225. doi: 10.1080/07391102.2016.1174737.
7. Kent K. P., Oltrogge L. M., Boxer S. G. Synthetic Control of Green Fluorescent Protein J Am Chem Soc, 2009, vol. 131, pp. 15988-15989. doi: 10.1021/ja906303f.
8. Wu M., Hancock R. E. Interaction of the Cyclic Antimicrobial Cationic Peptide Bactenecin with the Outer and Cytoplasmic Membrane, J Biol Chem, 1999, vol. 274, pp. 29-35. doi: 10.1074/jbc.274.1.29.
9. Abraham M. J., Murtola T., Schulz R., Páll S., Smith J. C., Hess B., Lindahl E.GROMACS: High performance molecular simulations through multi-level parallelism from laptops to supercomputers. SoftwareX, 2015, vol. 1, pp. 19-25. doi: 10.1016/j.softx.2015.06.001.
10. Battistutta R., Negro A., Zanotti, G. Crystal structure and refolding properties of the mutant F99S/M153T/V163A of the green fluorescent protein. Proteins, 2000, vol. 41, pp. 429-437. doi: 10.1002/1097-0134 (20001201) 41.
11. Melnik T. N., Povarnitsyna T. V., Glukhov A. S., Melnik B. S. Multi-state proteins. Approach allowing experimental determination of the formation order of structure elements in the green fluorescent protein. PloS ONE 2012. 7 (11): e48604. doi: 10.1371/journal.pone.0048604.
12. Li X, Romero P, Rani M, Dunker A K, Obradovic Z (1999) Predicting Protein Disorder for N-, C-, and Internal Regions. Genome informatics Workshop on Genome Informatics 10:30-40
13. Romero P, Obradovic Z, Li X, Garner E C, Brown C J, Dunker A K (2001) Sequence complexity of disordered protein. Proteins 42 (1): 38-48
14. Peng K, Vucetic S, Radivojac P, Brown C J, Dunker A K, Obradovic Z (2005) Optimizing long intrinsic disorder predictors with protein evolutionary information. J Bioinform Comput Biol 3 (1): 35-60
15. Obradovic Z, Peng K, Vucetic S, Radivojac P, Dunker A K (2005) Exploiting heterogeneous sequence properties improves prediction of protein disorder. Proteins 61 Suppl 7:176-182
16. Peng K, Radivojac P, Vucetic S, Dunker A K, Obradovic Z (2006) Length-dependent prediction of protein intrinsic disorder. BMC Bioinformatics 7:208
17. Xue B, Dunbrack R L, Williams R W, Dunker A K, Uversky V N (2010) PONDR-FIT: a meta-predictor of intrinsically disordered amino acids. Biochimica et biophysica acta 1804 (4): 996-1010

18. Dosztanyi Z, Csizmok V, Tompa P, Simon I (2005) IUPred: web server for the prediction of intrinsically unstructured regions of proteins based on estimated energy content. Bioinformatics 21 (16): 3433-3434
19. Mészáros B, Erdos G, Dosztányi Z. (2018) IUPred2A: context-dependent prediction of protein disorder as a function of redox state and protein binding. Nucleic Acids Res. 2018 July 2; 46 (W1): W329-W337
20. Tsien R. Y. The green fluorescent protein. *Annu Rev Biochem,* 1998, vol. 67, pp. 509-544. doi: 10.1146/annurev.biochem.67.1.509.
21. Stepanenko O. V., Stepanenko O. V., Kuznetsova I. M., Verkhusha V. V., Turoverov K. K. Beta-Barrel Scaffold of Fluorescent Proteins: Folding, Stability and Role in Chromophore Formation. *Int Rev Cell Mol Biol,* 2013, vol. 302, pp. 221-278. doi: 10.1016/B978-O-12-407699-0.00004-2.

What is claimed is:

1. A composition comprising a modified green fluorescent protein (GFP) molecule and a bactenecin, wherein the bactenecin consists of SEQ ID NO: 1 and replaces at least a part of a central α-helix region of a GFP molecule comprising SEQ ID NO: 2, and wherein the modified GFP molecule comprises the amino acid substitutions F8D, I167D, and Q177E, which confer stability to the composition.

2. The composition of claim 1, wherein the modified GFP molecule is capable of fluorescence.

3. A nucleic acid encoding a modified GFP molecule and a bactenecin, wherein the bactenecin consists of SEQ ID NO: 1 and replaces at least a part of a central α-helical moiety of a GFP molecule comprising SEQ ID NO: 2, and wherein the modified GFP molecule comprises the amino acid substitutions G8D, I167D, and Q177E, which confer stability to the composition.

4. A cell encoding the nucleic acid of claim 3.

* * * * *